United States Patent [19]
Dory

[11] Patent Number: 4,658,828
[45] Date of Patent: Apr. 21, 1987

[54] APPARATUS FOR EXAMINING AND LOCALIZING TUMORS USING ULTRA SOUNDS, COMPRISING A DEVICE FOR LOCALIZED HYPERTHERMIA TREATMENT

[76] Inventor: Jacques Dory, 91, rue des Molveaux, 77450 Coupvray-Esblay, France

[21] Appl. No.: 728,905

[22] Filed: Apr. 30, 1985

[30] Foreign Application Priority Data

May 3, 1984 [FR] France ................................ 84 06877

[51] Int. Cl.$^4$ .......................... A61B 8/00; A61N 5/00
[52] U.S. Cl. ...................................... 128/660; 128/399
[58] Field of Search ...................... 128/24 A, 399, 804, 128/660

[56] References Cited

U.S. PATENT DOCUMENTS

| | | | |
|---|---|---|---|
| 3,237,623 | 3/1966 | Gordon | 128/24 A |
| 3,958,559 | 5/1976 | Glenn et al. | 128/24 A |
| 4,315,514 | 2/1982 | Drewes et al. | 128/660 X |
| 4,434,341 | 2/1984 | Busby et al. | 128/804 X |
| 4,441,486 | 4/1984 | Pounds | 128/24 A |
| 4,526,168 | 7/1985 | Hassler et al. | 128/24 A |

FOREIGN PATENT DOCUMENTS 2126901 4/1984 United Kingdom ................ 128/399

OTHER PUBLICATIONS

Cooper et al., "A Scanning, Focused Ultrasound . . . ", Pro. 10th Ann. NW Bio Eng Conf., Hanover, N.H., Mar. 1982, pp. 97-100.

Primary Examiner—Lee S. Cohen
Attorney, Agent, or Firm—William A. Drucker

[57] ABSTRACT

A hyperthermia applicator comprises a generator of a focused ultrasonic beam comprising a main high frequency electric wave emitter and a main piezoelectric transducer and an echography device comprising an auxiliary high frequency electric pulse generator associated with an auxiliary piezoelectric transducer which generates an ultrasonic examination beam sweeping the zone to be treated. During a main treatment and checking operating mode, the focused beam is emitted by the main transducer energized by the main emitter during periodic time intervals separated by shorter time intervals. During the shorter time intervals, the examination beam is emitted and echographic images are formed.

4 Claims, 4 Drawing Figures

4,658,828

APPARATUS FOR EXAMINING AND LOCALIZING TUMORS USING ULTRA SOUNDS, COMPRISING A DEVICE FOR LOCALIZED HYPERTHERMIA TREATMENT

BACKGROUND OF THE INVENTION

Conventional echography apparatus are obviously used for examining tumours inside the body by forming an image thereof on the screen of a cathode ray tube.

As is known, it is also possible to obtain destruction of the cells—in particular malignant cells—by subjecting them to a more or less extended temperature rise. The cells to be destroyed must for example be brought to about 45° C. in a well controlled way while avoiding reaching excessive temperatures which could cause serious burns around the lesion. The technical problem to be resolved consists then both in controlling the amount of energy and the localization thereof.

With the different prior processes (use of ultrahigh frequencies, infrared radiation, and others) superficial tumours can be treated but deeper tissues cannot be reached.

The invention proposes applying ultra sounds to the examination and hyperthermia treatment and provides an apparatus which combines the three functions of localizing the zone to be treated, of treating by raising the temperature in a well controlled way in a well defined restricted region within this zone and simultaneously checking the results of the treatment.

SUMMARY OF THE INVENTION

The hyperthermia treatment apparatus of the invention combines a generator of a focused ultra sonic beam comprising a main high frequency electric wave emitter and a main piezoelectric transducer whose active surface is focusing, with an echography device comprising an auxiliary high frequency electric pulse generator associated with an auxiliary piezoelectric transducer and with means for causing the zone to be treated to be swept by the ultrasonic examination beam being generated by the auxiliary transducer; and with switching and adjusting means for causing, during main treatment and checking operation, the emission of said focused beam by the main transducer energized by the main emitter during periodic time intervals separated by shorter time intervals during which the emission of the examination beam and the formation of echographic images are carried out.

The apparatus advantageously comprises a first auxiliary locating operation mode during which only the periodic emission of the examination beam by the auxiliary transducer is effected and preferably a second auxiliary operating mode for checking the focal region, during which only the periodic emission of the focused beam is effected, but the main emitter is synchronized by the synchronization circuit of the auxiliary generator for echographic operation, the time intervals which separate the successive emission periods during the two auxiliary operation modes being substantially smaller than the intervals which separate the periods of emission of the focused beam during the main mode.

It follows from the foregoing that, during the auxiliary operating modes for obtaining accurate adjustments, the quality of the echographic image, either of the zone to be treated (locating mode) or of the focal region (mode for checking the restricted region), will be substantially better than during the treatment mode, during which the successive images of the zone to be treated will follow each other for example at intervals of the order of a second, which however allow the position of the focal region to be checked satisfactorily during treatment.

In a preferred embodiment, the auxiliary transducer is fixed to the spherical surface of the main transducer and thus, during movement of this latter for bringing the focal spot into successive restricted regions of the tumour, the auxiliary transducer will at all times supply an image of the treated region and of the zone which surrounds it, thus allowing a permanent check of the treatment to be effected easily and accurately.

BRIEF DESCRIPTION OF THE DRAWINGS

Other features and advantages of the invention will be clear from the following description.

In the accompanying drawings.

DESCRIPTION OF THE PREFERRED EMBODIMENT

Figure 2:
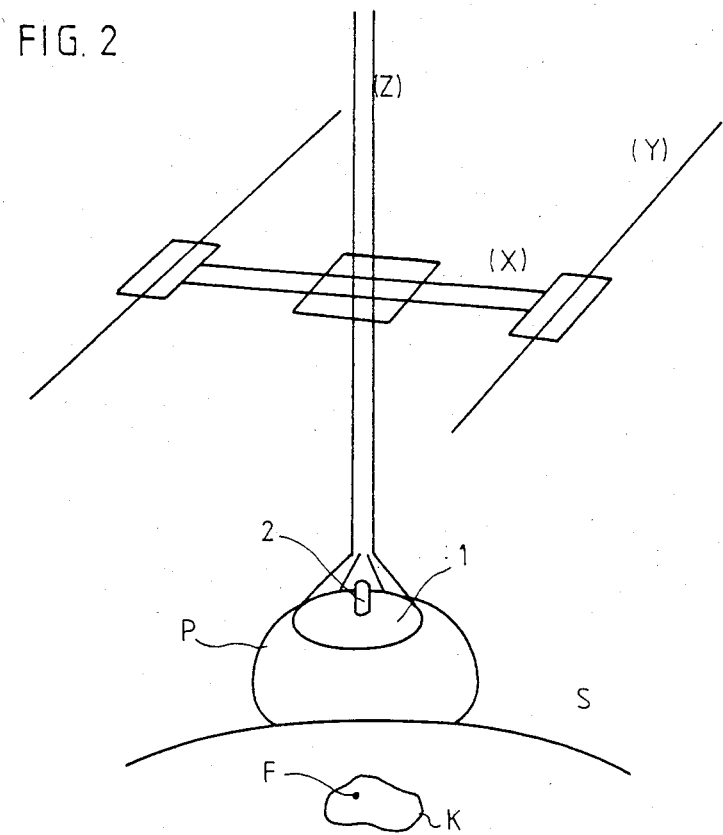
FIG. 2 shows schematically in perspective the main transducer and its mobile support device.

In FIG. 2 is shown a main transducer 1 in the form of spherical skull cap supported by a mount which allows it to move along three orthogonal axes X, Y and Z. This mount has been shown schematically, its construction being within the scope of a man skilled in the art. Along the axis of the spherical skull cap is disposed an auxiliary transducer 2 of a generally cylindrical shape which passes through skull cap 1 and is fixed thereto. A pocket of water P is placed between the skull cap 1 and the surface S of the body of the patient, who is assumed lying flat on a horizontal plane.

The skull cap 1 has for example a diameter of 200 to 300 mm and is formed from a large number (300 or 400) of piezoelectric elements 10, 11, etc ... (FIG. 1) isolated from each other and juxtaposed so as to form a mosaic. These elements are metallized on both faces, one of the metallizations being connected to ground and the other to connections for energization by a main emitter 3.

Figure 3:
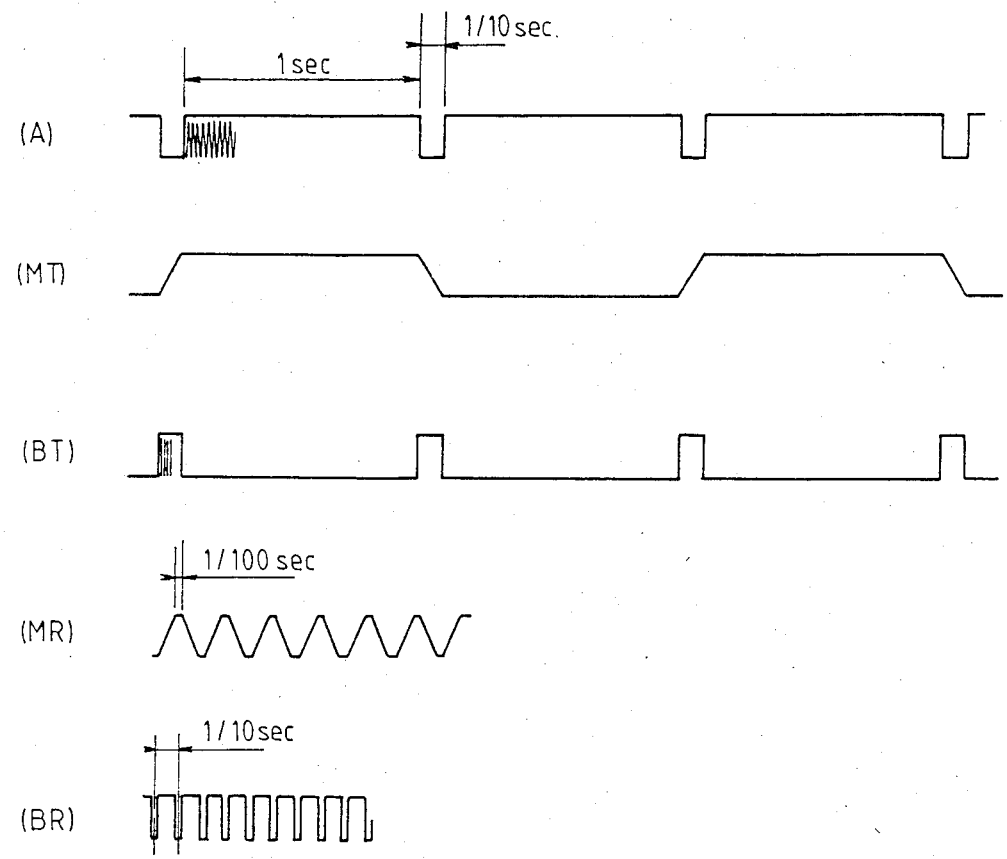
FIG. 3 shows the wave forms at different points of the circuits of the apparatus.

This latter delivers an electric signal A (FIG. 3) formed of high frequency wave trains (500 KHz for example) of a relatively low peak power (about 10 or a 100 watts for example), but of a relatively long duration (for example of the order of a second) separated by time intervals of the order of 1/10 second, the time required for the echography device to form an image. It is then a question of operating conditions using substantially continuous emission for the treatment. Such operating conditions may be obtained by means of emitters using power transistors. Preferably, the elements of transducer 1 will be divided up into groups each energized by a separate emitter (rectangle 4 symbolizing the assembly of these emitters), the elements of each group being spaced apart in the same circular zone of the spherical surface. By adjusting the relative phases of the emissions, it is possible to modify the energy distribution in the focusing region of the ultra sonic beam.

An input 31 to emitter 3 symbolizes an adjustment of the emitted power and an input 32 symbolizes an adjustment of the wave train duration. The focal spot formed in the center F of the sphere may, with this technique, be very small (diameter of 2 or 3 mm for example) and have a position which is strictly fixed for a given position of the transducer.

Figure 1:
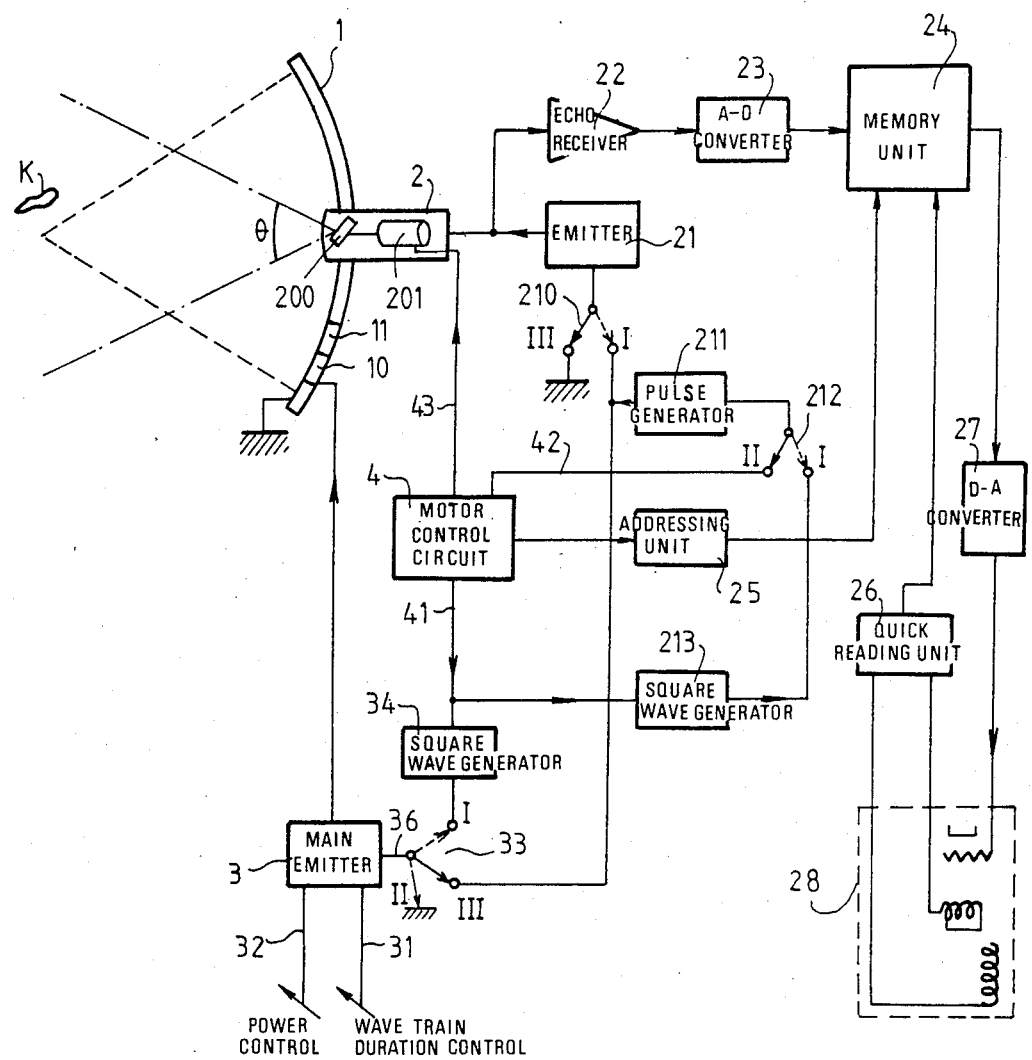
FIG. 1 is the general diagram of a hyperthermia apparatus according to a preferred embodiment of the invention.

In FIG. 1 it can be seen that the auxiliary transducer 2 is itself connected both to a high frequency electric pulse emitter 21 and to a reception amplifier 22 followed by an analog-digital converter 23, itself followed by a memory 24. Emitter 21 is synchronized by a pulse generator 211 which delivers 256 pulses during each of the successive time intervals of 1/10 second. To each of these time intervals corresponds a complete sweep of a given angular sector $\theta$ (FIG. 1) by the beam emitted by transducer 2 so the formation, in the sweep plane, of an image of the zone observed by the echography device.

Transducer 2 is advantageously of the type described in U.S. Pat. No. 4,418,698 granted on Dec. 31, 1983, for: "Ultrasonic scanning probe with mechanical sector scanning means", that is to say that it comprises an oscillating piezoelectric element 200 controlled by a motor 201, itself controlled by an electronic circuit which is shown symbolically by a rectangle 4. This electronic circuit provides control signals for the motor 201 housed inside the case of the transducer 2 and is adapted so that a complete oscillation of the motor corresponds to the above defined duration for forming an image (1/10 sec.).

In a first operating mode (treatment and checking) switch 210 is in position I as well as switches 212 and 33.

Figure 4:
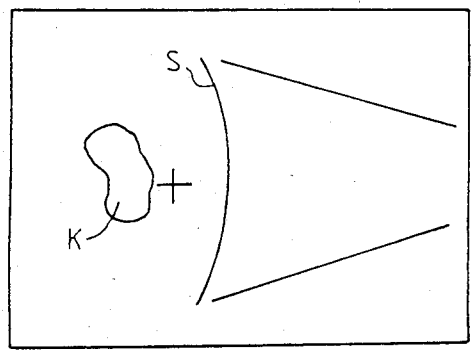
FIG. 4 illustrates the image obtained on the display screen which the apparatus comprises.

In position I of switches 33 and 212, generator 211 is synchronized by a first output 41 of circuit 4, and this latter is then adjusted, by means not shown, for generating at its output 43 connected to motor 201 signals having the wave form (MT) shown in FIG. 4. An image is swept then in 1/10 sec. and is followed by a time interval of 1 sec. during which the oscillating element 200 remains immobile, so that transducer 2 receives no echos.

During the intervals between the sweep periods, a circuit 34 generates square waves of 1 sec. which serve for synchronizing emitter 3 whereas, during the sweep periods, a circuit 213 generates square waves of 1/10 sec. which serve for synchronizing the generator 211.

Thus, in this operating mode, transducer 1 generates an ultra-sonic beam under substantially continuous operating conditions whereas the echography device forms an image every second in the intervals between the wave trains. At (BT) has been shown the wave forms of the signals then emitted by generator 211.

In a second operating mode (locating) with switch 210 in position I, switch 33 is in position II, so that emitter 3 is not synchronized and the focused ultrasonic beam is not emitted. Switch 212 is also in position II so that generator 211 is synchronized by a second output 42 of circuit 4 and this latter is adjusted so as to generate at its output 43 signals having the wave forms (MR) shown in FIG. 3. The 1/10 sec. sweeps are then separated by time intervals of 1/100 sec. only and the images are formed from echos coming from the reflection of the pulses generated by transducer 2. Generator 211 delivers the signals (BR).

In a third operating mode (checking the focal region), switch 210 is in position III, so that the emitter 21 and transducer 2 do not emit. Switch 212 is again in position II so that generator 211 is synchronized by the output 42 of circuit 4 and this latter is adjusted as in the second operating mode so that the 1/10 sec. sweeps are again separated by intervals of 1/100 sec. Switch 33 is in position III and consequently emitter 3 is now synchronized by the generator 211 which then delivers the signals (BR).

In this third operating mode, the echographic device is therefor formed by emitter 3, transducer 1 operating for emission and transducer 2 operating for reception. The result is that an image of the zone of concentration in the focal region of the energy emitted by the transducer 1 is obtained.

The echographic signals received at 22 in the first or third operating modes are, after analog-digital conversion at 23, stored line by line in memory 24, a writing addressing device 25, controlled by circuit 4, causing the respective deflection angles of the beam emitted and/or received by transducer 2 to correspond with the respective lines of the memory. A device 26 for rapid reading of the memory energizes the X and Y deflection coils of a cathode ray tube 28, so the brightness control electrode receives the corresponding contents from memory 24, transformed into an analog signal by a digital-analog converter 27.

The practical construction of all the circuits described and shown is within the scope of a man skilled in the art. The control circuit 4 may for example comprise a one shot multivibrator delivering square waves of a duration adjustable to 1/100 s or 1s depending on the operating mode and circuits for generating increasing and decreasing voltages of a 1/10 s duration, triggered off by said square waves.

The apparatus which has just been described operates as follows:

In the locating operating mode, the operator searches for and localizes the zone to be treated. The display device is adapted, in a way known per se, so as to materialize on the screen of the cathode ray tube (for example by means of a cross) the theoretical position of the focal spot in the sectional plane shown, which plane passes through the axis of symmetry of transducer 1. (It is a question of B type echography). The operator begins by moving transducer 1 along X, until the tumour appears clearly on the screen, then he moves it along Y and Z, until the cross coincides with the central region of the image of the tumour (K, FIG. 4). At this moment, the switches may be placed in position for checking the focal region: only this latter is then made visible on the screen, with a luminosity proportional to the corresponding energy concentration. Thus a representation is obtained of what the distribution of the energy of the treatment wave will be, which allows the adjustments to be checked and perfected.

During treatment, the apparatus only supplies one image per second, but this rate is sufficient for substantially permanently checking the position of the focal spot.

It is clear that the apparatus described allows the evolution of the tumour to be checked after each treatment sequence. It is evident that different modifications may be made thereto and even according to other embodiments, without departing from the scope and spirit of the invention.

What is claimed is:

1. Apparatus for ultrasonically heating a subject volume comprising:
   (i) a first transducer having a curved transmitting surface for generating a single first ultrasound beam focused in a restricted focal zone and drive means for excitig ultrasonic vibrations within the first transducer;

(ii) means for displacing the first transducer with respect to predetermined axes of coordinates successively to irradiate subject volume with said ultrasound beam focal zone;

(iii) a second transducer for generating a second ultrasound beam, said second transducer having an active surface which is substantially smaller than that of the transmitting surface of the first transducer, said second transducer having a point which is fixed with the first transducer during the displacement of the first transducer, and (iv) an echography device comprising said second transducer, electric pulse generator means coupled to said second transducer, means for effecting a scanning of an examination volume with the second ultrasound beam, receiver means coulped to said second transducer for receiving the echoes formed through reflexion of the second ultrasound beam on reflecting surfaces within the examination volume and image forming means coupled to the receiver means for displaying images of the examination volume, said focal zone being located in a predetermined relative position within the examination volume, and said image forming means further displaying a mark which materializes said predetermined position of the focal zone.

2. Apparatus as claimed in claim 1, wherein said first transducer is formed by a mosaic of piezoelectric elements isolated for each other and forming a spherical skill cap suported by said displacing means, said skull cap having a top, said displacing means being adapted for controlling the displacement of the first transducer along three orthogonal axes, whereas the second transducer is fixed to the top of said skull cap and said means for effecting a scanning of the second ultrasound beam provide a sectorial sweep of said second beam in a plane which passes through the axis of symmetry of said skull cap.

3. Apparatus for ultrasonically heating a subject volume comprising:

(i) a first transducer having a curved transmitting surface for generating a single first ultrasound beam focused in a restricted focal zone and drive means for exciting ultrasonic vibrations within the first transducer;

(ii) means for displacing the first transducer with respect to predetermined axes of coordinates successively to irradiate subject volume with said ultrasound beam focal zone;

(iii) a second transducer for generating a second ultrasound beam, said second transducer having an active surface which is substantially smaller than that of the transmitting surface of the first transducer, said second transducer having a point which is fixed with the first transducer during the displacement of the first transducer;

(iv) an echography device comprising said second transducer, electric pulse generator means coupled to said second transducer, means for effecting a scanning of an examination volume with the second ultrasound beam, receiver means coupled to said second transducer for receiving the echoes formed though reflexion of the second ultrasound beam on reflecting surfaces within the examination volume and image forming means coupled to the receiver means for diplaying images of the examination volume, said focal zone being located in a predetermined relative position within the examination volume, and said image forming means further displaying a mark which materializes said predetermined position of the focal zone;

(v) said drive means exciting ultrasonic vibrations within the first transducer during periodic time intervals which are separated by first blanks of substantially smaller duration;

(vi) said echography device further comprising means for controlling the generation of electric pulses by said generator means during second periodic time intervals having the same duration as said first blanks and separated by second blanks, and (vii) switchable synchronization means having first and second operating modes for effecting coincidence of each of said second blanks with said first time intervals and setting the drive means into operation during the first mode and for effecting coincidence of a plurality of said second time intervals and the associated second blanks with each of the first time intervals and setting the drive means out of operation during the second mode.

4. Apparatus fo ultrasonically heating a subject volume comprising:

(i) a first transducer having a curved transmitting surface for generating a single first ultrasound beam focused in a restricted focal zone and drive means for exciting ultrasonic vibrations within the first transducer;

(ii) means for displacing the first transducer with respect to predetermined axes of coordinates successively to irradiate subject volume with said ultrasound beam focal zone;

(iii) a second transducer for generating a second ultrasound beam, said second transducer having an active surface which is substantially smaller than that of the transmitting surface of the first transducer, said second transducer having a point which is fixed with the first transducer during the displacement of the first transducer;

(iv) an echography device comprising said first and second transducers, electric pulse generator means coupled to said second transducer, means for effecting a scanning of an examination volume with the second ultrasound beam, receiver means coupled to said second transducer for receiving the echoes formed through reflexion of an examination ultrasound beam on reflecting surfaces within the examination volume and image forming means coupled to the receiver means for displaying images of the examination volume, said focal zone being located in a predetermined relative position within the examination volume, and said image forming means further diplaying a mark which materializes said predetermined position of the focal zone;

(v) switchable synchronization means having first, second and third operating modes;

(vi) during said first and second operating modes, said drive means exciting ultrasonic vibrations within the first transducer during first periodic time intervals which are separated by first blanks of substantially smaller duration;

(vii) said echography device further compirsing means for controlling the generation of electric pulses by said generator means during second periodic time intervals having the same duration as said first blanks and separated by second blanks;

(viii) said synchronization means effecting coincidence of each of said second blanks with said first time intervals and setting the drive means into operation during the first mode and effecting coincidence of a plurality of said second time intervals and the associated second blanks with each of the time intervals and setting the drive means out of operation during the second mode; and (ix) said synchronization means discoupling said electric pulse generator means from the second transducer during said third operating mode and coupling said electric pulse generator means to the first transducer, whereas said electric pulse generator means is synchronized for effecting coincidence of a plurality of said second time intervals and the associated second blanks with each of the first time intervals.

* * * * *